United States Patent [19]

Mrozik et al.

[11] 4,201,861
[45] May 6, 1980

[54] ACYL DERIVATIVES OF C-076 COMPOUNDS

[75] Inventors: Helmut H. Mrozik, Matawan; Michael H. Fisher, Bridgewater; Peter Kulsa, Plainfield, all of N.J.

[73] Assignee: Merck & Co., Inc., Rahway, N.J.

[21] Appl. No.: 896,947

[22] Filed: Apr. 17, 1978

Related U.S. Application Data

[63] Continuation-in-part of Ser. No. 839,099, Oct. 3, 1977, abandoned.

[51] Int. Cl.$^2$ .................. C07H 17/08; C07D 493/22; C07D 491/22
[52] U.S. Cl. ............................ 536/17 A; 260/343.41; 544/150; 424/248.53; 424/279; 424/180
[58] Field of Search ..................... 260/343.41; 536/17; 544/79, 150

[56] References Cited
U.S. PATENT DOCUMENTS 3,950,360  4/1976  Auki et al. ................... 260/343.41
4,093,629  6/1978  Fisher ........................... 260/343.41

OTHER PUBLICATIONS

Mishima et al., Tetrahedron Letters 10, p. 711–714, 1975.
Jour. of Antibiotics, 29(6) Jun. 1976, p. 76–35 to 76–42 and p. 76–14 to 76–16.
Derwent Abstracts, 76268W/46 to Sankyo Co. Ltd.

Primary Examiner—Henry R. Jiles
Assistant Examiner—Jane T. Fan
Attorney, Agent, or Firm—David L. Rose; Harry E. Westlake

[57] ABSTRACT

Derivatives of C-076, a series of macrolides, are described in which the substituents are acyl groups. The acyl substituents may be aromatic of non-aromatic. The acyl derivatives are prepared by various procedures depending upon the particular C-076 compound being substituted. The compounds thus produced have profound anthelmintic, insecticidal, ectoparasiticidal and acaracidal activity and compositions for such uses are also disclosed.

16 Claims, No Drawings

ACYL DERIVATIVES OF C-076 COMPOUNDS

CROSS REFERENCE TO RELATED APPLICATIONS

This application is a continuation-in-part of our application Ser. No. 839,099, filed Oct. 3, 1977 now abandoned.

BACKGROUND OF THE INVENTION

The term C-076 is used to describe a series of compounds isolated from the fermentation broth of a C-076 producing strain of *Streptomyces avermitilis*. The morphological characteristics of the culture are completely described in copending U.S. patent application Ser. No. 772,601. The C-076 compounds are a series of macrolides with hydroxy substituents capable of being acylated. Some of the C-076 compounds have more than one hydroxy group which are capable of being acylated, and procedures have been developed for the selective acylation at the various positions. The acyl compounds thus produced have profound anthelmintic, insecticidal, ectoparasiticidal and acaracidal activity.

Based on taxonomic studies, the microorganisms capable of producing these C-076 compounds are of a new species of the genus *Streptomyces*, which has been named *Streptomyces avermitilis*. One such culture, isolated from soil is designated MA-4680 in the culture collection of Merck & Co., Inc., Rahway, New Jersey. A C-076 producing sample of this culture has been deposited in the permanent culture collection of the Permentation Section of the Northern Utilization Research Branch, U.S. Department of Agriculture at Peoria, Ill., and has been assigned the accession number NRRL 8165. A sample of NRRL 8165 has also been deposited, without restriction as to availability, in the permanent culture collection of the American Type Culture Collection at 12301 Parklawn Drive, Rockville, Md. 20852, and has been assigned the accession number ATCC 31,267.

The above microorganism is illustrative of a strain of *Streptomyces avermitilis* which can be employed in the production of the C-076 compounds. However, such description also embraces mutants of the above described microorganism. For example, those C-076 producing mutants which are obtained by natural selection or those producted by mutating agents including X-ray irradiation, ultraviolet irradiation, nitrogen mustard or like treatments are also included within the ambit of this invention.

One example of such an organism is a strain of *Streptomyces avermitilis* MA 4848 which was isolated after irradiation with ultraviolet light of *Streptomyces avermitilis* MA 4680. A lyophilized tube and a frozen vial of this culture has been deposited in the permanent culture collection of the American Type Culture Collection, and they have been assigned the accession numbers 31272 and 31271 respectively. Slightly higher fermentation yields of C-076 have been obtained using this frozen stock as inoculum.

SUMMARY OF THE INVENTION

The C-076 series of compounds have the following structure:

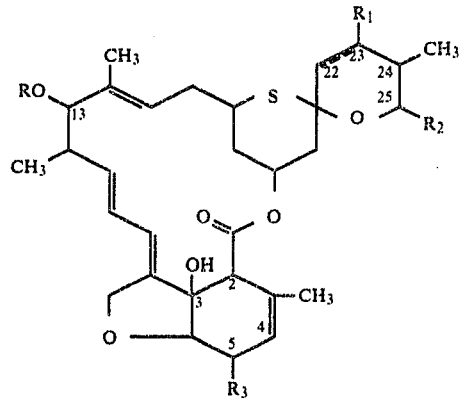

wherein R is the $\alpha$-L-oleandrosyl-$\alpha$-L-oleandrose group of the structure:

and wherein the broken line between $C_{22}$ and $C_{23}$ indicates a single or a double bond;

$R_1$ is hydroxy and is present only when said broken line indicates a single bond;

$R_2$ is iso-propyl or sec-butyl; and $R_3$ is methoxy or hydroxy.

There are eight different C-076 compounds and they are given the designations A1a, A1b, A2a, A2b, B1a, B1b, B2a, B2b based upon the structure of the individual compounds.

In the foregoing structural formula, the individual C-076 compounds are as set forth below.

|  | $R_1$ | $R_2$ | $R_3$ |
|---|---|---|---|
| A1a | Double bond | sec-butyl | —OCH$_3$ |
| A1b | Double bond | iso-propyl | —OCH$_3$ |
| A2a | —OH | sec-butyl | —OCH$_3$ |
| A2b | —OH | iso-propyl | —OCH$_3$ |
| B1a | Double bond | sec-butyl | —OH |
| B1b | Double bond | iso-propyl | —OH |
| B2a | —OH | sec-butyl | —OH |
| B2b | —OH | iso-propyl | —OH |

As is readily seen, all of the C-076 compounds have hydroxy groups at the 7-position and the 4"-position of the carbohydrate side chain. The 7-position hydroxy group, however, is resistant to acylation and under the conditions described herein, no 7-position acylation product having been isolated. Thus all of the compounds have at least one acylatable hydroxy group. In addition, the A2 and B1 series of compounds have a second acylatable hydroxy group and the B2 series of compounds has a third acylatable hydroxy group.

The carbohydrate side chain may also be hydrolyzed to remove one or both of the $\alpha$-L-oleandrose groups. In this case there would remain an acylatable hydroxy group at the 4' or 13-position with the removal of a single $\alpha$-L-oleandrose (monosaccharide) or both $\alpha$-L-oleandrose (aglycone) respectively.

The monosaccharide and aglycone derivatives are prepared by the treatment of the parent C-076 compound with acid. The outer α-L-oleandrose group is more easily removed than the α-L-oleandrose group directly bonded to the C-076 substrate thus facilitating the separate preparation of the monosaccharide and aglycone without contamination with the other reaction product.

The process employed for the removal of the C-076 carbohydrate group or groups is to put the C-076 starting material in solution in a mixture of from 0.01 to 10% acid in a non-nucleophylic water miscible solvent such as dioxane, tetrahydrofuran, dimethoxyethane, dimethylformamide, bis-2-methoxyethyl ether and the like, and from 0.1 to 20% water. The mixture is stirred for from 6 to 24 hours at room temperature to complete the reaction. Acids such as sulfuric, hydrochloric, hydrobromic, phosphoric, trifluoroacetic and trifluorosulfonic are acceptable. Sulfuric acid is preferred.

When lower acid concentrations are used such as from 0.01 to 0.1% are employed the monosaccharide is predominantly prepared. When higher concentrations of acid are employed, such as in the range of 1 to 10%, the aglycone is predominantly prepared. Intermediate concentrations of acid will tend to prepare mixtures of monosaccharide and aglycone which are generally separable using chromatographic techniques.

The monosaccharide may also be prepared by stirring the C-076 precursor for from 6 to 24 hours at room temperature in 1% sulfuric acid in isopropanol. In addition the aglycone can be prepared by stirring the C-076 precursor for from 6 to 24 hours at room temperature in 1% sulfuric acid in methanol. The acid in methanol. The other acids listed above may also be employed in this process. This process is preferred for use with the 2-series of C-076 compounds since some addition may be observed to the 22,23 double bond of the series of C-076 compounds with a 22,23 unsaturation. The desired monosaccharide or aglycone are isolated and purified using techniques known to those skilled in the art.

The acyl compounds of this invention are realized in the following structural formula:

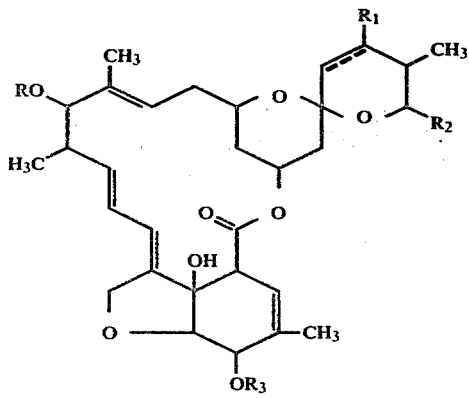

wherein the broken line indicates a single or a double bond;

$R_1$ is hydroxy or acyloxy and is present only when the broken line indicates a single bond;
$R_2$ is iso-propyl or sec-butyl;
$R_3$ hydrogen, methyl or acyl; and
R is hydrogen, acyl, α-L-oleandrosyl, 4'-acyl-α-L-oleandrosyl, 4'-(α-L-oleandrosyl)-α-L-oleandrosyl, 4''-acyl-4-(α-L-oleandrosyl)-α-L-oleandrosyl;
provided that at least one of the R, $R_1$, or $R_3$ groups contains an acyl group.

The foregoing acyl groups and the acyl portion of the acyloxy groups are: loweralkanoyl; substituted loweralkanoyl wherein the substituents are halogen, carboxy, loweralkoxycaronyl, amino, mono- or di-loweralkylamino, or loweralkanoylamino; unsaturated loweralkanoyl, loweralkoxycarbonyl, halogenated loweralkoxycarbonyl, benzoyl, or substituted benzoyl in which the substituents are halogen, nitro, alkyl, amino, hydroxy or alkoxy; carbamoyl and N-substituted and N,N-disubstituted carbamoyl wherein the substitution is loweralkyl, benzyl, hydroxyloweralkyl, or the carbomoyl nitrogen may be incorporated into a morpholine heterocycle. The acyloxy group at $R_1$ is defined as the above acyl groups bonded to the 23-position through an oxygen atom.

In the instant application the term "loweralkyl" is intended to include those straight or branched chain alkyl groups containing from 1 to 12 carbon atoms such as methyl, ethyl, propyl, isopropyl, butyl, pentyl, hexyl, decyl, dodecyl and the like.

The term "loweralkoxy" is intended to include those alkoxy groups containing from 1 to 6 carbon atoms such as methoxy, ethoxy, propoxy, isopropoxy, butoxy, tert-butoxy, pentoxy, hexoxy and the like.

The term "loweralkanoyl" is intended to include those alkanoyl groups containing from 2 to 12 carbon atoms such as acetyl, propionyl, butyryl, pentanoyl, hexanoyl, pivaloyl, octanoyl, decanoyl and the like.

"Unsaturated loweralkanoyl" is intended to include those alkanoyl groups containing from 3 to 12 carbon atoms and a double bond such as acryloyl, crotonoyl and the like.

The term "halogen" is intended to include the halogen atoms fluorine, chlorine, bromine, and iodine.

The carbamoyl groups is defined as the following:

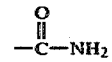

with optional substitution or disubstitutuion on the nitrogen atom.

The most preferred substitution is a loweralkanoyl group at the 4'' position, the 5-position, the 4'' and 5 positions or the 4'' and 23 positions. The acetyl and propionyl groups are the most preferred loweralkanoyl group.

The acylated compounds are prepared using acylation techniques in which the reaction conditions will vary, depending upon the reactivity of the hydroxy group being acylated. Where there is more than one hydroxy group to be acylated, different reaction conditions are employed to minimize the formation of mixtures.

The acylation reagents employed are generally the halide, preferably the chloride, of the above named acyl groups. Thus the acyl halide reagent in the case of the loweralkanoyl, substituted loweralkanoyl and unsaturated loweralkanoyl acyl groups would be the loweralkanoyl, substituted loweralkanoyl or unsaturated loweralkanoyl halide. Similarly the loweralkoxycarbonyl halide; benzoyl or substituted benzoyl halide; carbamoyl or substituted carbamoyl halide could be employed to form the respective acylated compound. The acyl haloformate, preferably the chloroformate is another successful acylation reagent.

In addition, in the case of the loweralkanoyl, substituted loweralkanoyl, benzoyl or substituted benzoyl groups, the acylation reagent could be in the form of the anhydride. In the case of reactions carried out with the halide reagents, it is often advantageous to include in the reaction mixture a basic compound capable of reacting with and neutralizing the hydrogen halide which is liberated during the course of the reaction. Tertiary amines are preferred such as triethylamine, pyridine, 4-dimethylamino pyridine, diisopropyl ethylamine and the like. The basic compound is required in equimolar amounts relative to the numbered moles of hydrogen halide being liberated, however excess amounts, even using the basic compound as a solvent, are not detrimental.

In the case of the A1 compounds, there is only a single hydroxy group, 4" hydroxy, which may be acylated. The formation of the monosaccharide or the aglycone still leaves only a single hydroxy group which may be acylated, that is the 4' or 13 hydroxy group.

In the case of the 4", 4' and 13 hydroxy groups of C-076 A1 compounds, the acylating reagent is dissolved in a suitable solvent, pyridine is preferred, and the acylating reagent added. The reaction is maintained at from 0° C. to room temperature for from 4 to 24 hours. The product is isolated using known techniques.

The A2 compounds have two available hydroxy groups, the 4"(4' or 13) or the 23 positions. The different hydroxy groups may be selectively acylated by controlling the reaction conditions.

The 4"(4' or 13) monoacyl compound may be prepared by using the reaction conditions described above for the A1 compound. Since the 23 hydroxy is less reactive than the 4"(4' or 13) position, mild reaction conditions (0° C.) will afford predominantly the monoacyl compound. Heating the reaction mixture at from room temperature to 100° C. for from 1 to 24 hours will produce the 4"(4' or 13), 23-diacyl compound. If the 23 monoacyl compound is desired, the diacyl compound is treated with aqueous base, such as sodium hydroxide, at room temperature for from 1 to 24 hours. The 4"(4' or 13) acyl group will be hydrolyzed leaving the 23 monoacyl compound.

The B1 compounds also have 2 available hydroxy groups: at the 4"(4' or 13) and the 5-positions. However, in this case the two hydroxy groups have similar reactivities. When the reaction of the acylating agent in pyridine is carried out at about room temperature for from 4 to 24 hours, the diacyl compound is recovered. When the reaction is carried out at 0° C. a mixture of the 4"(4' or 13) and 5 monoacyl compounds are recovered. To recover individual compounds, the mixture is placed on a chromatographic column or a preparative layer chromatographic plate of alumina or silica gel and the individual compounds are readily isolated. In addition, techniques such as high pressure liquid chromatography may be employed to separate mixtures of acylated compounds.

The B2 compounds have three hydroxy groups available for substitution: the 4"(4' or 13), 5 and 23 positions. The relative reactivity of the various hydroxy groups is the same as in the other series of compounds. Thus, the triacyl compound may be prepared by carrying out the reaction at from room temperature to 100° C. The 4"(4' or 13), 5 diacyl compound may be prepared by carrying out the reaction at no more than room temperature. At 0° C. a mixture of 4"(4' or 13), and 5 monoacyl compounds is recovered which is separable as described above. By varying the reaction conditions and sequence, and by hydrolyzing the undesired acyl groups, all combinations of mono and diacyl compound may be recovered. For example, to prepare the 23-acyl compound, the triacyl compound is hydrolyzed with aqueous base as described above to remove the 4"(4' or 13) and 5 acyl groups. Acylation of the 23 monoacyl compound at 0° C. will result in a mixture of the diacyl compounds which is readily separable.

The above described acyl compounds are isolated from the reaction mixture using techniques known to those skilled in this art.

The novel acylated compounds of this invention have significant parasiticidal activity as anthelmintics, insecticides, ectoparasiticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The acylated C-076 compounds of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep Lucilia sp., biting insects and such migrating dipterous larvae as Hypoderma sp. in cattle, Gastrophilus in horses, and Cuterebra sp. in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp. and the housefly *Musca domestica*.

The compounds are also useful against insect pests of stored grains such as Tribolium sp., Tenebrio sp. and of agricultural plants such as spider mites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture.

These compounds may be administered orally in a unit dosage such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the C-076 compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered an aminal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparations using solketal, glycerol-formal and aqueous parenteral formulations are also used. The active acylated C-076 compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting and sucking insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally, good results are obtained with our novel compounds by the oral administration of from about 0.001 to 10 mg. per kg. of animal body weight, such total dose being given at one time or in divided doses over a relatively short period of time such as 1-5 days. With the preferred compounds of the invention, excellent control of such parasites is obtained in animals by administering from about 0.025 to 0.5 mg. per kg. of body weight in a single dose. Repeat treatments are given as required to combat re-infections and are dependent upon the species of parasite and the husbandry techiques being employed. The techniques for administering these materials to animals are known to those skilled in the veterinary field. The compounds may also be administered in combination with other antiparasitic compounds or compounds with other biological activities to provide for a single treatment with a broadened spectrum of activity.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active acylated C-076 compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular acylated C-076 compound employed, the compounds of this invention are usually fed at concentrations between 0.00001 to 0.002% in the feed in order to achieve the desired antiparasitic result.

In using the compounds of this invention, the individual acylated C-076 components may be prepared and used in that form. Alternatively, mixtures of two or more of the individual acylated C-076 components may be used.

In the isolation of the C-076 compounds, which serve as starting materials for the instant processes, from the fermentation broth, the various C-076 compounds will be found to have been prepared in unequal amounts. In particular an "a" series compound will be prepared in a higher proportion than the corresponding "b" series compound. The weight ratio of "a" series to the corresponding "b" series is about 85:15 to 99:1. The differences between the "a" series and "b" series is constant throughout the C-076 compounds and consists of a butyl group and a propyl group respectively at the 25 position. This difference, of course, does not interfere with any of the instant reactions. In particular, it may not be necessary to separate the "b" components from the related "a" component. Separation of these closely related compounds is generally not practiced since the "b" compound is present only in a very small percent by weight, and the structural difference has negligible effects on the reaction processes and biological activities.

The C-076 compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The following examples are provided in order that the invention might be more fully understood; they are not to be construed as limitations of the invention.

The C-076 derivatives prepared in the following examples are generally isolated as amorphous solids and not as crystalline solids. They are thus characterized analytically using techniques such as mass spectrometry, nuclear magnetic resonances and the like. Being amorphous, the compounds are not characterized by sharp melting points, however the chromatographic and analytical methods employed indicate that the compounds are pure.

EXAMPLE 1

C-076 Ala 4"-O-Acetate

A. 0.8 Mg. of C-076 Ala is combined with 3 drops of dry pyridine and 2 drops of acetic anhydride. The reaction mixture is allowed to stand stoppered for 2 days. The solution is transferred to a small flask and washed with benzene. The benzene layer is concentrated in vacuo, diluted and concentrated twice more with benzene. A thin layer chromatographic analysis on silica gel using 5% methanol in chloroform reveals only a single spot which is different from the starting material. Preparative layer chromatography on silica gel plates using 10% tetrahydrofuran in chloroform also reveals a single spot with an Rf of 0.5.

B. A solution of 27. mg. of 4-dimethylaminopyridine in 1 ml. of methylene chloride is prepared and a separate solution of 0.208 ml. of acetic anhydride in 10 ml. of methylene chloride is prepared. 0.5 Ml. of each solution is added to 10 mg. of C-076 Ala, mixed well and allowed to stand at room temperature overnight. The reaction mixture is diluted to 4 ml. with methylene chloride and 0.5 ml. of water is added and shaken. The layers are separated and the organic layer is dried over magnesium sulfate and evaporated to dryness under a stream of nitrogen. Benzene is added and the solution is lyophilized affording 10 mg. of an off-white fluffy solid. Preparative layer chromatography on silica gel eluting with 10% tetrahydrofuran in chloroform affords 8.2 mg. of a fluffy, off-white solid, which nuclear magnetic resonance and mass spectrographic analysis reveals to be C-076 Ala 4"-O-acetate.

EXAMPLE 2

C-076 A2a 4"-O-Propionate

25 Mg. of C-076 A2a is combined with 15 drops of dry pyridine and cooled in ice while 5 drops of propionic anhydride is added. The reaction mixture is stoppered, mixed well and allowed to stand in an ice bath overnight. The reaction mixture is diluted with ether and benzene and shaken with some ice water. The layers are separated and the organic layer is dried over magnesium sulfate. The solvent is evaporated under a stream of nitrogen, benzene is added and the solution is lyophilized affording 20 mg. of a white solid. Preparative layer chromatography on silica gel eluting with 5% tetrahydrofuran in chloroform affords 16.6 mg. of a white solid which is analysed by nuclear magnetic resonance and mass spectrometry as C-076 A2a 4"-O-propionate.

EXAMPLE 3

4"-O-(Methoxycarbonyl) C-076 A2a

25 Mg. of C-076 A2a is combined with 0.25 ml. of dry methylene chloride, 0.5 ml. of dry triethylamine and 25 mg. of 4-dimethylamino pyridine. A separate solution is prepared by adding 0.2 ml. of methylchlorocarbonate dropwise to 3 ml. of dry methylene chloride at room temperature. 0.3 Ml. of the solution is added to the first solution and the combined solutions stoppered and stirred at room temperature for 5 hours, whereupon another 0.3 ml. of the methylchlorocarbonate solution is added and the reaction mixture allowed to stir at room temperature overnight. The reaction mixture is diluted with 7.5 ml. of ether and washed 4 times with 3 ml. of water. The organic layer is dried over magnesium sulfate, concentrated in vacuo and dried under high vacuum affording a solid material. Preparative layer chromatography on silica gel of the solid material, eluting twice with 5% tetrahydrofuran in chloroform affords 8.2 mg. of a white solid which mass spectrometry and nuclear magnetic resonance reveals to be 4"-O-(methoxycarbonyl) C-076 A2a.

EXAMPLE 4

4"-O-(p-Bromobenzoyl) C-076 A2a

250 Mg. of C-076 A2a is dissolved in a mixture of 2.5 ml. of dry methylene chloride, 5 ml. of dry triethylamine and 250 mg. of 4-dimethylaminopyridine. The solution is stirred at room temperature while 3 ml. of a solution formed from 500 mg. of p-bromobenzoyl chloride and 3 ml. of dry methylene chloride is added. Another 10 ml. of methylene chloride is added and the reaction mixture is stirred for 2 hours. The reaction mixture is diluted with 200 ml. of ether and washed with a saturated sodium bicarbonate solution, 2.5 N hydrochloric acid solution, saturated sodium bicarbonate solution and water. The organic layer is dried over magnesium sulfate, concentrated in vacuo and dried under high vacuum affording 425 mg. of a yellow solid. Preparative layer chromatography on silica gel of the solid material, eluting twice with 5% isopropanol in benzene and once with 5% tetrahydrofuran in chloroform affords 277.4 mg. of a pale yellow solid, which mass spectrometry and nuclear magnetic resonance reveal to be 4"-O-(p-bromobenzoyl)-C-076 A2a.

EXAMPLE 5

4"-23-Di-O-(2,2,2-Trichloroethoxycarbonyl)-C-076 A2a

A solution of 10 mg. of C-076 A2a is combined with 10 drops of dry pyridine, mixed well and 2 drops of 2,2,2-trichloroethylchlorocarbonate is added affording an immediate off-white precipitate. The reaction mixture is allowed to stand for one and a half hours. The reaction mixture is combined with ice, mixed well, allowed to stand for 20 minutes and the liquid decanted from a gummy residue. The residue is washed once with water and dissolved in 4 ml. of ether. The ether is dried over magnesium sulfate and evaporated to dryness under a stream of dry nitrogen 1.5 ml. of benzene is added and the solution is lyophilized. The lyophilized solid is dissolved in methylene chloride and purified with preparative layer chromatography on silica gel eluting with 10% tetrahydrofuran in chloroform affording 10.2 mg. of an off-white solid which mass spectrometry and nuclear magnetic resonance reveal to be 4",23 di-O(2,2,2-trichloroethoxycarbonyl) C-076 A2a.

EXAMPLE 6

C-076 A2a 4"-O-Benzoate

10 Mg. of C-076 A2a is dissolved in 0.4 ml. of dry pyridine and 50 mg. of benzoic anhydride is added and the reaction vessel immersed in an oil bath at 100° C. and stirred for 4 hours. The solution is allowed to cool to room temperature and combined with benzene and lyophilized affording a lyophilized powder. Preparative layer chromatography on silica gel eluting with 10% tetrahydrofuran in chloroform affords 7.8 mg. of a fluffy white solid which mass spectrometry and nuclear magnetic resonance reveal to be C-076 A2a 4'-benzoate.

EXAMPLE 7

4"-O-(Chloroacetyl) C-076 A2a

10 Mg. of C-076 A2a is dissolved in 0.15 ml dry pyridine, cooled in an ice bath and 30 mg. of chloroacetic anhydride is added maintaining the temperature at 0° C. The reaction mixture is worked up using lyophilization and preparative layer chromatography techniques as previously described affording 6.4 mg. of a white powder which nuclear magnetic resonance and mass spectrometry reveal to be 4"-O-(chloroacetyl) C-076 A2a.

EXAMPLE 8

204"-O-(Carbomethoxypropionyl) C-076 A2a

10 Mg. of C-076 A2a is dissolved in 0.25 ml. of a solution prepared from 108 mg. of 4-dimethylaminopyridine and 0.15 ml. of diisopropylethylamine brought to a volume of 0.5 ml. with methylene chloride. The solution is cooled in an ice bath and 0.1 ml. of methylene chloride containing 5 mg. of carbomethoxypropionyl chloride is added. The reaction mixture is stoppered and allowed to stand in an ice bath for 20 minutes. The reaction mixture is diluted with methylene chloride, washed 3 times with water, dried over magnesium sulfate and evaporated to dryness in a stream of nitrogen. Preparative layer chromatography on silica gel eluting with 15% tetrahydrofuran in chloroform affords 6.9 mg. of a white solid which mass spectrometry reveals to be 4"-O-(carbomethoxypropionyl) C-076 A2a.

EXAMPLE 9

4"-O-(N-Acetylglycyl) C-076 A2a

30 Mg. of C-076 A2a is combined with 0.75 ml. of a solution consisting of 216 mg. of dimethylaminopyridine and 0.3 ml. of diisopropylethylamine brought to a total volume of 10 ml. with methylene chloride. This solution is cooled in an ice bath and a solution of 13.4 mg. of N-acetylglycyl chloride in 0.3 ml. of methylene chloride is added dropwise. The reaction mixture is stirred in an ice bath for ½ hour and at room temperature for 1½ hours. The reaction mixture is worked up as previously described using preparative layer chromatography on silica gel eluting with 15% tetrahydrofuran in chloroform affording 3.2 mg. of a white solid which mass spectrometry reveals to be 4"-O-(N-acetylglycyl) C-076 A2a.

EXAMPLE 10

4"-O-(p-Nitrophenoxycarbonyl) C-076 A2a and 4",23-di-O-(p-Nitrophenoxycarbonyl) C-076 A2a 100 Mg. of C-076 A2a is dissolved in 2.5 ml. of a solution of 108 mg. of 4-dimethylaminopyridine and 0.15 ml. of diisopropylethylamine brought to a volume of 5 ml. with dry methylene chloride. The reaction mixture is stirred in an ice bath and another 1.0 ml. of methylene chloride is added along with 66 mg. of p-nitrophenylchloroformate. The reaction mixture is stirred at room temperature overnight and diluted with 50 ml. of ether and washed 4 times with pH 5 buffer, dried over magnesium sulfate and concentrated in vacuo. The residue is chromatographed on silica gel chromatography plates eluting twice with 3% tetrahydrofuran in chloroform affording two separate areas of product. There is obtained 40.6 mg. of 4",23-di-O-(p-nitrophenoxycarbonyl) C-076 A2a and 69.8 mg. of 4"-O-(p-nitrophenoxycarbonyl) C-076 A2a.

EXAMPLE 11

C-076 A2a 4"-O-Acetate

Following the procedure of Example 1, 5 mg. of C-076 A2a is acetylated affording 4.4 mg. of a product which is demonstrated by mass spectrometry and nuclear magnetic resonance to be C-076 A2a 4"-O-acetate.

EXAMPLE 12

C-076 A2a 4",23-di-O-acetate

A. 10 Mg. of C-076 A2a is acetylated in 0.5 ml. of pyridine and 0.25 ml. acetic anhydride at 100° C. for 2 hours. The reaction mixture is worked up using preparative layer chromatography on silica gel as previously described affording 5.9 mg. of a fluffy white solid which mass spectrometry and nuclear magnetic resonance reveal to be C-076 A2a 4",23-di-O-acetate.

B. The reaction part A above is repeated on 400 mg. of C-076 A2a affording 420 mg. of product which is identified analytically as C-076 A2a 4",23-di-O-acetate.

EXAMPLE 13

C-076 A2A 4",23-di-O-acetate

Following the procedure of Example 1, 5.2 mg. of C-076 B1a is acetylated with 10 drops of pyridine and 6 drops of acetic anydride affording, after preparative layer chromatography and lyophilization, 5.2 mg. of a white fluffy solid which mass spectrometry indicates is C-076 B1a 4",5-di-O-acetate.

EXAMPLE 14A

C-076 B1a 4'',O-Acetate and C-076 B1a 4'',5-Di-O-Acetate

20 Mg. of C-076 B1a is dissolved in 12 drops of pyridine, cooled in an ice bath and combined with 4 drops of acetic anhydride. The reaction mixture is maintained in an ice bath for 2½ hours, chilled benzene is added, the reaction mixture freeze dried and the solid material chromatographed on silica gel plates eluting with 10% isopropanol in benzene. The product with the highest Rf is identified by mass spectrometry as C-076 B1a 4'',5-di-O-acetate, 4.7 mg. is obtained. The mext most advanced spot is identified by mass spectrometry as C-076 B1a 4'',O-acetate; 9.3 mg. is obtained.

EXAMPLE 14B

C-076 B1a 4'',O-Acetate and C-076 B1a 4'',5-Di-O-Acetate

The procedure of Example 14A is repeated using 500 mg. of C-076 B1a, 4.5 ml. of dry pyridine and 0.5 ml. of acetic anhydride. The reaction mixture is maintained at 0° C. for 4 hours. The reaction mixture is added to a stirred ice-water mixture to obtain a white precipitate, which is filtered and the filter cake dissolved in ether. The ether layer washed twice with saturated sodium bicarbonate, once with water, dried over magnesium sulfate and concentrated in vacuo. The residue is placed on a column of 33 g. of silica gel and eluted with 20% ethyl acetate in methylene chloride. The fractions are collected at a rate of 4 ml. per minute and 20 ml. fractions are collected. Fractions 1–6 are discarded. Fractions 7–16 are combined and concentrated affording 122.8 mg. of a white solid. High pressure liquid chromatographic analysis of this fraction indicates the product to be C-076 B1a 4'',5-di-O-acetate. Fractions 19–45 are also collected and treated in a similar manner affording 175.1 mg. of a white solid identified as C-076 B1a 4'',0-acetate.

EXAMPLE 15

C-076 B1a 4'',O-Acetate and C-076 B1a 4'',5-Di-O-Acetate 4.1 G. of C-076 B1a is dissolved at 37 ml. of dry pyridine and cooled in an ice bath. 4.1 Ml. of acetic anhydride is added and the reaction mixture stirred in an ice bath for 3½ hours. The reaction mixture is added to a stirred mixture of 350 ml. of ice and water to obtain a white precipitate which is filtered, washed with water and dissolved in 300 ml. of ether. The ether solution is washed twice with 25 ml. portions of saturated sodium bicarbonate and once with 25 ml. of water. The ether is dried over magnesium sulfate and concentrated to dryness in vacuo affording 4.5 g. of a white solid. The above procedure is repeated on 5.0 g. of C-076 B1a to afford 5.5 g. of a white solid, 2.6 g. of which is combined with the above 4.5 g. and the combined 7.1 g. of solid is placed on a high pressure liquid chromatography column and eluted with 25% ethyl acetate in methylene chloride at 300 ml. per minute. A forecut of 1.8 l. is taken and discarded. The next fraction of 1.6 l. is evaporated to dryness affording 1.50 g. of C-076 B1a 4'',5-di-O-acetate. Fraction 3 (300 ml.) contains 100 mg. of a mixture of C-076 B1a 4'',5-di-O-acetate, and C-076 B1a 4''-O-acetate. Fractions 4,5 and 6 (3.0 l.) are combined and evaporated affording 3.3 g. of C-076 B1a 4''-O-acetate.

EXAMPLE 16

C-076 B1a 4''-O-Acetate and C-076 B1a 4'',5-Di-O-Acetate and C-076 B1a 5-O-Acetate 2 G. of C-076 B1a is dissolved in 18 ml. of dry pyridine and cooled in an ice bath. 2 Ml. of acetic anhydride is added and the reaction mixture stirred in an ice bath for 3 hours and 45 minutes. The reaction mixture is added dropwise to 300 ml. of a stirred ice and water mixture affording a white precipitate. The suspension is filtered, and the solid material washed twice with water and dissolved in 200 ml. of ether. The ether layer is washed twice with 20 ml. portions of saturated sodium bicarbonate and once with a 20 ml. portion of water. The ether is dried over magnesium sulfate, and evaporated to dryness in vacuo affording 2.0 g. of a white solid. The solid material is placed on a column of 130 g. of silica gel and eluted with 20% ethyl acetate in methylene chloride taking 20 ml. fractions at a rate of 7 ml. per minute. Fractions 7–44 are combined and evaporated to afford 413.9 mg. of a solid identified as C-076 B1a 4'',5-di-O-acetate. Fractions 45–48 contains less than 20 mg. of a mixture and is discarded. Fractions 49–115 are combined and contain 809.8 mg. of C-076 B1a 4''-O-acetate. Fractions 116–190 contain 246.5 mg. of a mixture which is further purified using preparative layer chromatography on silica gel plates eluting with 8% tetrahydrofuran in chloroform to afford 180.9 mg. of a solid which is again chromatographed on similar plates eluting with 10% tetrahydrofuran in chloroform affording 136.2 mg. of of C-076 B1a 5-O-acetate.

EXAMPLE 17

C-076 B1b 4''-O-Acetate

10 Mg. of C-076 B1b is dissolved in 9 drops of dry pyridine and cooled in an ice bath while 1 drop of acetic anhydride is added. The product is isolated by pouring the reaction mixture onto ice water as described in Example 17 and preparatively chromatographing the solid material on silica gel plates eluting with 8% tetrahydrofuran in chloroform affording 0.9 mg. of a material identified as C-076 B1b 4'',5-di-O-acetate and 3.2 mg. of C-076 B1b 4''-O-acetate.

EXAMPLE 18

C-076 B2a 4'',O-acetate and C-076 B2a 4'',5-Di-O-acetate

200 Mg. of C-076 B2a is dissolved in 2.1 ml. of dry pyridine and cooled in an ice bath. 0.7 Ml. of acetic anhydride is added and the reaction mixture stirred for one hour. The reaction mixture is poured onto 50 ml. of ice and water with stirring. The precipitate is filtered and the solid material dried, dissolved in ether and the ether washed with water and dried over magnesium sulfate. The ether layer is evaporated to dryness and the solid material purified by preparative layer chromatography on silica gel plates eluting with 10% isopropanol in benzene affording 115.7 mg. of C-076 B2a 4''-O-acetate and 27.7 ml. of C-076 B2a 4'',5-di-O-actetate identified by mass spectrometry.

EXAMPLE 19

C-076 B2a 4″,5-Di-O-Acetate

20 Mg. of C-076 B2a is dissolved in 12 drops of dry pyridine and cooled in an ice bath. 4 Drops of acetic anhydride is added and the reaction mixture is allowed to stand at 0° C. overnight. The reaction mixture is combined with benzene and lyophilized and the solid material purified by preparative layer chromatography on silica gel plates eluting with 5% tetrahydrofuran in chloroform affording 20.8 mg. of a white solid identified by mass spectrometry as C-076 B2a 4″,5-di-O-acetate.

EXAMPLE 20

C-076 B2a 4″,5,23-Tri-O-Acetate

20 Mg. of C-076 B2a is dissolved in 0.8 ml. of dry pyridine and 0.4 ml. of acetic anhydride is added. The reaction mixture is stirred at 100° C. for 2 hours. Upon cooling, benzene is added and the mixture is lyophilized affording 22.6 mg. of a light brown solid which is purified by preparative layer chromatography on silica gel plates eluting with 5% tetrahydrofuran in chloroform affording 13.5 mg of C-076 B2a 4″,5,23-tri-O-acetate.

EXAMPLE 21

C-076 B1a 4″,O-Propionate

25 Mg. of C-076 B1a is dissolved in 15 drops of dry pyridine and cooled in an ice bath. 5 Drops of propionic anhydride is added and the reaction mixture stirred in an ice bath for 2½ hours. The reaction mixture is added to ice chips and mixed well and ether is added. The ether layer is separated and the aqueous layer re-extracted with ether. The combined ether layers are washed with water, dried and evaporated under a stream of nitrogen affording 25 mg. of an off white solid. The solid material is purified by preparative layer chromatography on silica gel plates eluting with 10% tetrahydrofuran in chloroform affording 4.6 mg. of C-076 B1a 4″-O-propionate.

EXAMPLE 22

4″,O-(p-Chlorobenzoyl) C-076 B1a and 5-O-(p-Chlorobenzoyl)C-076 B1a

10 Mg. of C-076 B1a is dissolved in 0.2 ml. of triethylamine and 10 mg. 4-dimethylaminopyridine is added. 0.1 Ml. of dry methylene chloride is added in order to dissolve all of the reactants. 0.02 Ml. of p-chlorobenzoyl chloride is added. The reaction mixture is allowed to stand at room temperature for 1½ hours. 6 Ml. of methylene chloride and 0.6 ml. of saturated sodium bicarbonate solution is added and shaken. The aqueous layer is removed and 0.6 ml. of water is added, shaken and separated. The ether layer is dried over magnesium sulfate and evaporated to dryness under a stream of nitrogen. Preparative layer chromatography on silica gel plates of the residue eluting with 5% isopropanol in benzene affords 5.1 mg. of a fluffy white solid identified by mass spectrometry as 4″,O-(p-chlorobenzoyl) C-076 B1a. There is also obtained 6.2 mg. of a fluffy white solid identified by mass spectrometry as 5-O-(p-chlorobenzoyl) C-076 B1a. The structures are confirmed by nuclear magnetic resonance.

EXAMPLE 23

4″-O-(3-Carbomethoxypropionyl) C-076 B1a

10 Mg. of C-076 B1a is dissolved in 0.25 ml. of a solution of 108 mg. of 4-imethylaminopyridine and 0.15 ml. of diisopropylethylamine in 5 ml. of dry methylene chloride. The mixture is cooled in an ice bath and 0.1 ml. of methylene chloride containing 5 mg. of carbomethoxypropionyl chloride is added. The reaction mixture is stirred at room temperature for 15 minutes and a few ice chips are added. The reaction mixture is diluted with methylene chloride, washed 3 times with water and the organic layer dried over magnesium sulfate and evaporated under a stream of nitrogen affording 10 mg. of a yellow solid. Preparative layer chromatography on silica gel plates of the residue, eluting with 5% tetrahydrofuran in chloroform affords 4.5 mg. of a solid material identified by nuclear magnetic resonance and mass spectrometry as 4″-O-(3-carbomethoxypropionyl) C-076 B1a.

EXAMPLE '$

C-076 B2a 4″-O-Propionate

Following the procedure of Example 21 using 25 mg. of C-076 B2a there is obtained, after preparative layer chromatography on silica gel plates eluting with 10% tetrahydrofuran in chloroform, 5.1 mg. of a white solid identified by mass spectrometry as C-076 B2a 4″-O-propionate.

EXAMPLE 25

4″-O-(p-Chlorobenzoyl) C-076 B2a

Following the procedure of Example 22 using the same scale there is obtained after preparative layer chromatography on silica gel plates eluting with 5% tetrahydrofuran in chloroform 6.4 mg. of a fluffy white solid identified by mass spectrometry as 4″-O-(p-chlorobenzoyl) C-076 B2a.

EXAMPLE 26

C-076 A2a Aglycone 13,23-Di-O-Acetate

25 Mg. of C-076 A2a aglycone is dissolved in 0.4 ml. of dry pyridine, mixed and combined with 0.2 ml. of acetic anhydride and stirred in an oil bath at 100° C. for 2½ hours. The reaction mixture is cooled and combined with ice and shaken with ether. The ether layer is separated and the aqueous layer extracted twice more with ether. The ether layers are combined washed with water, dried and evaporated to dryness under a stream of nitrogen. The residue is purified by preparative layer chromatography on silica gel plates eluting with 8% tetrahydrofuran in chloroform affording 21.2 mg. of an off white solid identified by mass spectrometry as C-076 A2a aglycone 13,23-di-O-acetate.

EXAMPLE 27

13,O-(p-Chlorobenzoyl) C-076 A2a Aglycone and 23, O-(p-Chlorobenzoyl) C-076 A2a Aglycone 21 Mg. of C-076 A2a aglycone is dissolved in 0.28 ml. of a solution prepared from 82 mg. of dimethylaminopyridine, 0.12 ml. of diisopropylethylamine and 2.5 ml. of dry methylene chloride. The mixture is stirred and cooled in an ice bath. Dropwise, 0.1 ml. of a solution of 0.065 mg. of p-chlorobenzoyl chloride in 1 ml. of dry methylene chloride is added and the reaction mixture stoppered and stirred in a ice bath for 2 hours. The reaction mixture is diluted with 12 ml. of ether and washed successively with 1.5 ml. portions of water, 2.5 normal HCl, saturated sodium bicarbonate and water. The ether layer is dried over magnesium sulfate and evaporated to dryness under a stream of nitrogen. Benzene is added and the solution lyophilized affording 40 mg. of a yellowish solid. The solid material is purified by preparative layer chromatography on silica gel plates eluting with 5% tetrahydrofuran in chloroform affording 1.2 mg. of a white solid identified by mass spectrometry as 23-O-(p-chlorobenzoyl) C-076 A2a aglycone and 12.4 mg. of a white solid also identified by mass spectrometry as 13-O-(p-chlorobenzoyl) C-076 A2a aglycone.

EXAMPLE 28

C-076 A2a Aglycone 13-O-Benzoate

10 Mg. of C-076 A2a aglycone is dissolved in 0.3 ml. of dry pyridine and combined with 20 mg. of benzoic anhydride and heated in an oil bath at 100° C. for 16 hours. The reaction mixture is cooled, benzene is added and the solution lyophilized. The residue is purified by preparative layer chromatography on silica gel plates eluting with 3% isopropanol and benzene affording 8.3 mg. of a white solid identified by mass spectrometry and nuclear magnetic resonance as C-076 A2a aglycone 13,O-benzoate.

EXAMPLE 29

13, 23-Di-O-(p-Bromobenzoyl) C-076 A2a Aglycone

10 Mg. of C-076 A2a aglycone is combined with 0.1 ml. of dry methylene chloride, 0.2 ml. of dry triethylamine and 10 mg. of 4-dimethylaminopyridine. Dropwise, 20 ml. of p-bromobenzoyl chloride in 0.12 ml. of methylene chloride is added followed by an additional 0.4 ml. of methylene chloride to aid in dissolving the reagents. The reaction mixture is stirred at room temperature for 2 days and diluted with 10 ml. of ether and extracted once with saturated sodium bicarbonate, once with 0.5 ml. of 2.5 normal hydrochloric acid, again with sodium bicarbonate solution and then with dilute sodium chloride solution. The ether layer is dried over magnesium sulfate and evaporated to dryness under a stream of nitrogen. Preparative layer chromatography on silica gel plates eluting with 2.5% tetrahydrofuran in chloroform affords 9.5 mg. of a white solid identified by mass spectrometry and nuclear magnetic resonance as 13,23-di-O-(p-bromobenzoyl) C-076 A2a aglycone.

EXAMPLE 30

C-076 A2a Monosaccharide 4'-O-acetate

25 Mg. of C-076 A2a monosaccharide in 12 drops of dry pyridine is cooled in an ice bath and combined with 4 drops of acetic anhydride. The reaction mixture is stirred in an ice bath for 2 hours. Ice and water is added and the mixture extracted twice with ether and the combined ether extracts washed with water, dried over magnesium sulfate and evaporated to dryness under a stream of nitrogen. Benzene is added and the solution is lyophilized. Preparative layer chromatography on silica gel plates eluting with 10% tetrahydrofuran in chloroform affords 13.0 mg. of a white solid identified by mass spectrometry and nuclear magnetic resonance as C-076 A2a monosaccharide 4'-O-acetate.

EXAMPLE 31

4"-O-(p-chlorobenzoyl) C-076 A2a Monosaccharide

25 Mg. of C-076 A2a monosaccharide is dissolved in 0.25 ml. of a solution prepared from 82 mg. of dimethylaminopyridine and 0.12 ml. of diisopropylethylamine in 2.5 ml. of methylene chloride. The reaction mixture is cooled and combined with a 0.1 ml. solution derived from 0.65 ml. of p-chlorobenzoyl chloride and 1 ml. of dry methylene chloride. The reaction mixture is stirred in an ice bath for 25 minutes. 10 Ml. of chilled ether is added and the reaction mixture washed with 2 ml. each of water, 2.5 N hydrochloric acid, saturated sodium bicarbonate solution and water. The ether layer is dried over magnesium sulfate and evaporated in a stream of nitrogen. Preparative layer chromatography on silica gel plates eluting with 5% isopropanol in benzene affords 18.5 mg. of a white powder identified by mass spectrometry as 4'-O-(p-chlorobenzoyl) C-076 A2a monosaccharide.

EXAMPLE 32

C-076 B1a Monosaccharide 4"-O-Acetate and C-076 B1a Monosaccharide 4'-5-Di-O-Acetate 25 Mg. of C-076 B1a monosaccharide in 12 drops of pyridine is stirred and cooled in an ice bath and combined with 4 drops of acetic anhydride. The reaction mixture is stoppered and stirred in an ice bath for 75 minutes. 50 Ml. of ice water is added and the mixture is filtered and the solid material washed with water and dissolved in 60 ml. of ether. The ether layer is washed with water, dried over magnesium sulfate and evaporated to dryness in vacuo affording 25 mg. of a solid material. The solid material is purified by preparative layer chromatography on silica gel plates eluting with 5% tetrahydrofuran in chloroform affording 2.2 mg. of C-076 B1a monosaccharide 4'-5-di-O-acetate and 3.8 mg. of C-076 B1a monosaccharide 4'-O-acetate identified by mass spectrometry.

EXAMPLE 33

4'-O-(p-Chlorobenzoyl) C-076 B1a Monosaccharide

25 Mg. of C-076 B1a monosaccharide is dissolved in 0.25 ml. of a solution derived from 82 mg. of dimethylaminopyridine, 0.12 ml. of diisopropylethylamine in 2.5 ml. of methylene chloride. The mixture is stoppered and stirred in an ice bath and combined with 0.1 ml. of a solution derived from 0.65 ml. of p-chlorobenzoyl chloride and 1 ml. of dry methylene chloride. The reaction mixture is stirred in an ice bath for 40 minutes. 10 Ml. of ether is added and the mixture washed with 2 ml. each of water, 2.5 N Hydrochloric acid, saturated sodium bicarbonate solution and water. The ether layer is dried over magnesium sulfate and evaporated to dryness affording 30 mg. of a pale yellow solid. The solid material is purified by preparative layer chromatography on silica gel plates eluting with 4% tetrahydrofuran in chloroform affording 3.2 mg. of a white solid identified by mass spectrometry and nuclear magnetic resonance as 4'-O-(p-chlorobenzoyl) C-076 B1a monosaccharide.

EXAMPLE 34

C-076 A2a 4''-Octanoate

25 Mg. (0.028 moles) of C-076 A2a is dissolved in 0.5 ml. of methylene chloride containing 13.7 mg. of 4-dimethylamino pyridine and 14.5 mg. of diisopropyl ethylamine. This solution is cooled in an ice bath and 0.1 ml. a solution of methylene chloride containing 13.7 mg. of octanoyl chloride is added. The reaction is stirred for 40 minutes. Ice chips are added and the mixture stirred until they melted. The mixture is then extracted twice with ether the combined organic layers washed with water dried over magnesium sulfate and evaporated to dryness under a stream of nitrogen. Preparation layer chromatography on silica gel, eluting with 3% tetrahydrofuran, 0.3% ethanol in methylene chloride affords 20.5 mg. of a solid substance which mass spectrometry confirms is C-076 A2a 4''-octanoate.

EXAMPLE 35

C-076 A2a 4''-privalate

Following the procedure of Example 34 using pivaloyl chloride in place of octanoyl chloride, there is obtained C-076 A2a 4''-pivalate.

PREPARATION 1

C-076 A1a Aglycone

100 Mg. of C-076 A1a is dissolved in 5 ml. of dioxane stirred and added at room temperature to a mixture of 0.1 ml. of concentrated sulfuric acid, 1.9 ml. of methanol and 3.0 ml. of dioxane. The reaction mixture is stirred overnight at room temperature. 473 Mg. of solid sodium bicarbonate is added and the mixture stirred for 20 minutes. 3 Ml. of water is added and stirred for an additional 10 minutes. The reaction mixture is concentrated and 40 ml. of chloroform is added and shaken. The aqueou layer is separated and extracted with 5 ml. of chloroform. The organic layers are combined and washed once with dilute sodium chloride solution, dried over magnesium sulfate and evaporated to dryness in vacuo. One-half of the residue is placed on 5 preparative layer chromatography silica gel plates and eluted with 2% methanol in chloroform affording 4 bands of material. The remainder of the material was run on 2 preparative layer chromatography plates eluting with 2% methanol in chloroform affording 4 bands similar to the first series. The second fastest bands are removed from each of the plates combined, extracted and evaporated to dryness in vacuo and rechromatographed on a preparative layer chromatography silica gel plate eluting with 3% tetrahydrofuran and chloroform affording 9.4 mg. of a fluffy white solid which is identified by mass spectrometry as C-076 A1a aglycone.

PREPARATION 2

C-076 A2a Aglycone

2 G. of C-076 A2a is combined with 40 ml. of a 1% (volume/volume) solution of concentrated sulfuric acid in methanol. The reaction mixture is stirred at room temperature for 17 hours and diluted with 300 ml. of chloroform. The mixture is washed once with 30 ml. of saturated sodium bicarbonate solution, once with 30 ml. saturated sodium chloride solution, dried over magnesium sulfate and evapoerated to dryness in vacuo. 5 Ml. of methanol is added to the residue and allowed to stand at room temperature overnight. Cooling of the mixture in ice causes the slow precipitation of crystals. A supernatent is removed and the solid crystals washed twice with 1 ml. of cold methanol affording 340 mg. of a white solid. The mother liquor and washings are evaporated down to a volume of about 2 ml. and allowed to stand affording an additional crop to crystals. 630 Mg. of a white solid is obtained which is combined with the first batch of crystals and 8 ml. of methanol and evaporated to a volume of 2.5 ml. and allowed to stand for several hours. 910 Mg. of an off white solid is obtained which mass spectrometry identifies as C-076 A2a aglycone.

PREPARATION 3

C-076 A2a Monosaccharide

500 Mg. of C-076 A2a is dissolved in 10 ml. of a solution of 0.1 ml. of concentrated sulfuric acid and 9.9 ml. of isopropanol. The reaction mixture is stirred at room temperature overnight. 125 Ml. of chloroform is added and the mixture washed once with 10 ml. of saturated sodium bicarbonate and once with 10 ml. of water. The organic layer is dried over magnesium sulfate and evaporated to dryness in vacuo affording a pale yellow solid material which is dissolved in chloroform and placed on 5 preparative layer chromatography silica gel plates and eluted twice with 2% benzene in ethylacetate. The slower moving major fraction contains 367 mg. of a white powder after lyophilization from benzene which mass spectrometry and 300 MHz nuclear magnetic resonance indicates is C-076 A2a monosaccharide.

PREPARATION 4

C-076 B1a Monosaccharide and C-076 B1a Aglycone 2.5 Ml. of a solution consisting of 0.5 ml. of water 0.5 ml. concentrated sulfuric acid and 9.0 ml. of dioxane is added and the reaction mixture stirred at room temperature for 17 hours. 50 Ml. of ether is added followed by 25 ml. of saturated aqueous sodium bicarbonate solution. The two layer mixture is shaken, the aqueous layer separated and the organic layer washed with water, dried and evaporated to dryness in vacuo. Benzene is added to the residue and the benzene layer is dried and lyophilized affording 60 mg. of yellow material. The material is placed on a preparative layer chromatography silica gel plate and eluted with chloroform tetrahydrofuran in the volume ratio of 9:1 and 2 bands are observed with an Rf of 0.15 and 0.35. 300 MHz nuclear magnetic resonance identifies the two spots as C-076 B1a monosaccharide and C-076 B1a aglycone respectively. 16 Mg. of each fraction is obtained.

PREPARATION 5

C-076 B1a Monosaccharide

100 Mg. of C-076 B1a is dissolved in 5.0 ml. of tetrahydrofuran and stirred at room temperature while 5.0 ml. of a cold aqueous solution of 10% sulfuric acid (volume/volume) is added dropwise with stirring. The reaction mixture is stirred at room temperature for 18 hours. 75 Ml. of methylene chloride and 25 ml. of saturated aqueous sodium bicarbonate is added and the layers shaken and separated. The organic layer is washed with aqueous sodium chloride solution and an equal volume of water. The organic layer is dried and evaporated to dryness in vacuo affording 70 mg. of a colorless oil. High pressure liquid chromatography identifies the residual oil as C-076 B1a monosaccharide.

PREPARATION 6

C-076 B2a Aglycone

2 G. of C-076 B2a is combined with 40 ml. of a 1% solution of concentrated sulfuric acid in methanol (volume/volume). The reaction mixture is stirred at room temperature for 17 hours. 300 Ml. of chloroform is added followed by 30 Ml. of an aqueous saturated sodium bicarbonate solution. The layers are separated and the organic layer washed with 30 ml. of saturated sodium chloride solution, dried over magnesium sulfate and evaporated to dryness in vacuo. 5 Ml. of methanol is added to dissolve the residue and the mixture allowed to stand at room temperature and then cooled in an ice bath whereupon crystallization occurred. The supernatant is removed and the residue washed twice with 1 ml. portions of cold methanol and the solid crystals dried overnight and then in vacuo at 35° C. affording 1.0 g. of white crystals. A second crop is obtained by evaporating the mother liquors to a volume of 2 ml. and allowing to stand overnight at room temperature. 2 Ml. of methanol is added and the mixture aged in an ice bath affording 140 mg. of a yellow solid. The two solid fractions are combined and dissolved in boiling methanol, about 30 ml. of methanol is required. The solution is filtered hot and concentrated to a volume of about 20 ml. in vacuo whereupon solids begin to precipitate. The solution is filtered hot and the solid materials washed with methanol affording 340 mg. of a white solid. The filtrates are boiled down to a volume of about 8 ml. and set aside to crystallize at room temperature affording 433 mg. of a white solid. Mass spectrometry shows the two fractions to be identical and to be identified as C-076 B2a aglycone.

PREPARATION 7

C-076 B2a Monosaccharide and C-076 B2a Aglycone

20 Mg. of C-076 B2a is combined with 4 ml. of a solution prepared by combining 0.1 ml. of concentrated sulfuric acid and 9.9 ml. of isopropanol.

The reaction mixture is stirred at room temperature for 16 hours. 189 Mg. of sodium bicarbonate is added followed by a few drops of water. The volume is reduced to about ½ and 30 ml. of chloroform and 3 ml. of water is added and the mixture shaken. The layers are separated and the aqueous layer extracted with an additional 5 ml. of chloroform.

The organic layers are combined, washed once with dilute sodium chloride solution, dried over sodium sulfate and magnesium sulfate and evaporated to dryness in vacuo. The residue is placed on two preparative layer silica gel chromatography plates and eluted twice with 5% tetrahydrofuran in chloroform. 4 Bands of material are observed and individually removed from the preparative chromatography plates. The slowest band affords 7.3 mg. of a white solid which is identified by mass spectrometry monosaccharide. The next slowest band affords 1.3 mg. of a white solid and it is identified by mass spectrometry as C-076 B2a aglycone.

PREPARATION 8

A 250 ml. baffled Erlenmeyer flask containing 50 ml. of the following medium:

| | |
|---|---|
| Lactose | 2.0% |
| Distiller's solubles | 1.5% |
| Autolyzed yeast, Ardamine pH | 0.5% |
| pH - before sterilization | 7.0 | is inoculated with the contents of one frozen vial of *Streptomyces avermitilis* MA 4848 and incubated on a rotary shaker at 28° C. for 24 hours at 150 RPM.

10 Ml. of the above fermentation media is employed to inoculate 500 ml. of the same medium as above in a 2 liter baffled Erlenmeyer flask. The fermentation media is incubated at 150 RPM on a rotary shaker at 28° C. for 24 hours.

All of the foregoing media is employed to inoculate 467 liters of the following media in a 756 liter stainless steel fermentor:

| | |
|---|---|
| Lactose | 2.0% |
| Distiller's solubles | 1.5% |
| Autolyzed yeast, Ardamine pH | 0.5% |
| Polyglycol 2000 | 0.32 ml./liter |
| pH - before sterilization | 7.0 |

The fermentation media is incubated at 28° C. for 40 hours with an air flow 10 cubic feet per minute and an agitation rate 130 RPM.

230 Liters of the above media is employed to inoculate 4,310 liters of the following medium in a 5,670 liter stainless steel fermentor:

| | |
|---|---|
| Dextrose | 4.5% |
| Peptonized milk | 2.4% |
| Autolyzed yeast, Ardamine pH | 0.25% |
| Polyglycol 2000 | 2.5 ml./liter |
| pH - before sterilization | 7.0 |

The fermentation continues for 144 hours at 26° C. with an air flow rate of 54.3 cubic feet per minute and agitation of 120 RPM.

The fermentation media are filtered and the mycelial filter cake washed with about 550 liters of water, the filtrate and washings are discarded. The filter cake is agitated with about 1500 liters of acetone for about one hour and filtered. The filter cake is washed with a mixture of about 150 liters of acetone and 40 liters of deionized water affording about 2000 liters of extract.

The foregoing fermentation and extraction is repeated on the same scale affording a further 2000 liters of acetone extract which is combined with the first extract and evaporated to a volume of about 800 liters. The pH of the concentrate is adjusted to about 4.7 with concentrated hydrochloric acid and combined with about 800 liters of methylene chloride. The combined solvents are agitated for about 4 hours and separated. The aqueous layer is combined with an additional 800 liters of methylene chloride and agitated for about 4 hours. The layers are separated and each methylene chloride extract separately treated with about 10 kilograms of Super-Cel and filtered. Both extracts are evaporated to a combined volume of about 60 liters.

PREPARATION 9

The 60 liter solution of C-076 in methylene chloride of the previous example is concentrated to dryness in vacuo and the residue is combined 3 times with 60 liter portions of methanol and evaporated to dryness to remove any residual methylene chloride. The final methanol concentrate volume is approximately 36 liters. The methanol solution is stored overnight and filtered. The filter cake is washed with 40 liters of fresh methanol and the methanol filtrates and washings are combined. The methanol solution is combined with 95 liters of ethylene glycol and 130 liters of heptane. The 2 layer solution is agitated for 5 minutes and the lower layer (ethylene glycol and methanol) is separated. The heptane solution is washed with a mixture of 20 liters of ethylene glycol and 6.3 liters methanol. After five minutes of agitation, the lower layer is separated and combined with the first ethylene glycol/methanol extract. An equal volume of water (approximately 150 liters) containing 79 g. of salt per liter is added to the ethylene glycol/methanol extracts. This solution is extracted with 150 liters of ethyl ether with agitation for 5 minutes. The ether layer is washed with 75 liters of water ($\frac{1}{2}$ volume) and agitated for 5 minutes and the layers separated. This procedure is repeated an additional 2 times (the final water wash contains 20 g. of salt per liter) affording a final ether layer volume of 110 liters. The ether layer is concentrated in vacuo, to a mimimum volume, keeping the temperature less than 25° C. 40 Liters of methylene chloride is added to the residue and the solution is evaporated to dryness. This procedure is repeated and the final residue concentrated in vacuo at 50° C. to dryness.

PREPARATION 10

A 30 centimeter diameter column is prepared with a layer of 34 kilograms of activated alumina followed by a layer of 34 kilograms of activated carbon in a solution of methylene chloride. The residue from the previous example is dissolved in methylene chloride to a volume of 34 liters and applied to the column and eluted with 34 liters of methylene chloride. These fractions are discarded. A 3% solution of isopropanol and methylene chloride (20.8 liters of isopropanol and 660 liters of methylene chloride) is applied to the column and eluted in approximately 200 liter fractions. The combined isopropanol and methylene chloride fractions are evaporated in vacuo at a bath temperature of about 60° C. to a volume of about 20 liters. The bath temperature is reduced to about 45° C. and the extract is evaporated to dryness in vacuo. The residue is dissolved in 10 parts methylene chloride, 10 parts hexane and one part methanol to a final volume of 15 liters. This solution is applied directly to the Sephadex LH-20 column of the next example.

PREPARATION 11

A 30 centimeter diameter column is prepared in methanol with 36 kilograms of Sephadex LH-20 (available from Pharmacia Fine Chemicals, 800 Centennial Avenue, Piscataway, N.J. 08854) and washed with a solvent consisting of 10 parts methylene chloride, 10 parts hexane and one part methanol. One-fourth of the C-076 solution of Example 10 is applied to the column and the column eluted at a rate of 250 ml. per minute. Two 20 liter forecuts are collected and discarded followed by 20 two liter rich cuts (identified as fractions 1-20), followed by a single 20 liter tail cut, which is discarded. Fractions 1-8 are found to contain the C-076 A compounds and fractions 9-20 are found to contain the C-076 B compounds.

PREPARATION 12

The process of Preparation 11 is repeated on the same scale three more times and all of the fractions containing the C-076 B components (fractions 9-20) are combined and evaporated to dryness, affording 818 g. of crude mixed C-076 B components. The sample is found to contain 55% C-076 B1 and 39% of C-076 B2. 680.5 G. of this sample is dissolved in 2 liters of methylene chloride and placed in a 22 liter three neck round bottom flask followed by the addition of 13.6 liters of methanol. The methylene chloride is removed by distillation. 13.6 Liters of ethylene glycol is added as the methanol is being distilled under reduced pressure. The rate of distillation is maintained such that the temperature of the solution did not go below 65° C. When the addition of the ethylene glycol is complete, the solution is allowed to cool at 5° C. for sixteen hours. The crystals are filtered and washed with 1 liter of cold ethylene glycol. The crystals are then redissolved in 2 liters of methylene chloride the solution placed in a 22 liter three necked round bottom flask. The procedure described above is repeated twice. The first time 12.5 liters each of methanol and ethylene glycol is employed and the second time 13.6 liters each of methanol and ethylene glycol is employed. The final crystals are washed with 1 liter of cold ethylene glycol and 1 liter of water. The crystals are dissolved in 4 liters of water and dried by filtering through sodium sulfate. The benzene solution is concentrated to a volume of 2 liters and lyophilized affording 241.2 gm. of a white powder consisting of 98% C-076 $B_1$ and 1% of C-076 $B_2$.

The mother liquors (22 liters) from the first two crystallizations above are combined and diluted with 22 liters of water. The aqueous solution is extracted with 60 liters of toluene and again with 15 liters of toluene. The toluene extract is then washed with 48 liters of water. The organic phase is filtered through Super-Cel to remove any residual water and evaporated affording 336 gm. of solid material consisting of 79% C-076 $B_2$ and 16% C-076 $B_1$ compounds.

PREPARATION 13

In the four Sephadex LH-20 columns of the procedure of Preparation 11, fractions 1-8 contain the C-076 A compounds and are combined. By HPLC analysis the mixture is found to contain 252 g. of C-076 A2a, 16 g. of A2b, 94 g. of A1a and 24 g. of A1b. The material is dissolved in a solvent system consisting of hexane:toluene:methanol in the proportion of 6:1:1 and applied to the Sephadex LH-20 column of the same dimensions as the one used in Preparation 11 in the above solvent. Fractions are collected at the rate of 250 ml. per minute and a 20 liter forecut is collected and discarded. Further elution affords 2 additional 20 liter forecuts which are also discarded and 50 four liter rich cuts which contain C-076 A compounds. Fractions 3-8 are found to contain predominately C-076 A1 components (40.2 g. A1a and 6.7 g. A1b), and fractions 29-36 are found to contain C-076 A2 compounds (117.2 g. A2a and 7.35 g. of A2b). Fractions 9-28 contain a mixture of C-076 A1 and A2 compounds.

PREPARATION 14

A sample of 150 g. of C-076 B1 from Preparation 12 is dissolved in 3 liters of a solvent mixture of hexane:toluene:methanol in the ratio of 3:1:1. The solution is passed through a column of Sephadex LH-20 (of the same dimensions as the one used in Preparation 11) in the above solvent taking fractions at the rate of 250 ml. per minutes. After two 20 liter portions of the solvent mixture are collected and discarded, forecut of 10 liters is taken and discarded. Then 30 richcuts of 2 liters each are taken. Fractions 1-13 and 25-30 are discarded. Fractions 14-16 are combined and contain 80 g. of predominately C-076 B1a. Fractions 22-24 are combined and contain 6.7 g. of predominately C-076 B1b. Fractions 17-21 contain a mixture of C-076 B1a and B1b.

Fractions 17-21 above are combined and concentrated and passed through a Sephadex LH-20 column with the same solvent system as above. Three 20 liter forecuts are taken and discarded. Richcuts are then taken as follows: 5 cuts of 2 liters each (fractions 1-5); 20 cuts of 1 liter each (fractions 6-25); and 10 cuts of 2 liters each (fractions 26-35). Fractions 1-15 are discarded; fractions 16-21 contain 13.5 g of C-076 B1a and 0.4 g. of C-076 B1b; fractions 22-26 contain 44 g. of C-076 B1a and 0.13 g. of C-076 B1b; fractions 27-30 contain 10.2 g of C-076 B1a and 0.8 g. of C-076 B1b.

PREPARATION 15

A mixture of all 8 C-076 components are chromatographed on a high pressure liquid chromatography column 4 mm.×30 cm. packed with 10 micron μ Bondapak $C_{18}$ silica gel (available from Waters Associates Inc., Maple Street, Milford, Mass. 01757) eluting with 85:15 (v/v) methanol:water at a constant 40° C. At a flow rate of 1.2 ml. per minute all eight compounds are separated and the elution volumes, which under the foregoing constant conditions are characteristic of the individual compounds are as follows:

|  | Elution Volume (Ve) Ml |
|---|---|
| C-076 $B_2b$ | 5.90 |
| C-076 $B_2a$ | 6.52 |
| C-076 $A_2b$ | 7.12 |
| C-076 $A_2a$ | 7.88 |
| C-076 $B_1b$ | 8.36 |
| C-076 $B_1a$ | 9.60 |
| C-076 $A_1b$ | 10.24 |
| C-076 $A_1a$ | 11.88 |

The separation of C-076 "b" components from the respective "a" components is accomplished using techniques such as high pressure liquid chromatography. An absolute methanol solution of 30 microliters of a mixture of C-076 A1a and A1b, estimated to contain 30 micrograms of C-076 A1b is placed on a 3×250 mm. high pressure liquid chromatography column containing Spherisorb 5 micron ODS (available from Spectra Physics) as packing. The column is eluted with 85:15 methanol-water at a rate of 0.15 ml./min. The elution of the products are followed by observing the ultraviolet absorption of the eluent and collecting the individual components at the outlet of the UV monitor. 30 Micrograms of C-076 A1b is recovered in this manner.

What is claimed is:
1. A compound having the formula:

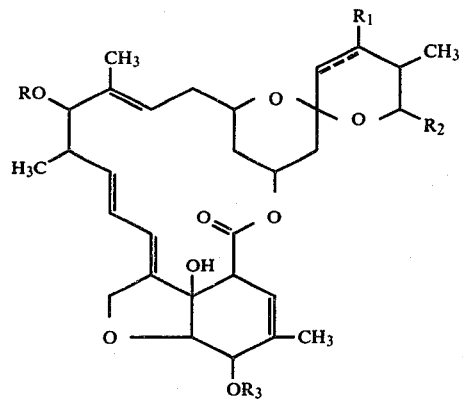

wherein the broken line indicates a single or a double bond;
$R_1$ is hydroxy or acyloxy and is present only when the broken line indicates a single bond;
$R_2$ is iso-propyl or sec-butyl;
$R_3$ is hydrogen, methyl or acyl; and
R is hydrogen, acyl, α-L-oleandrosyl, 4'-acyl-α-L-oleandrosyl, 4'-(α-L-oleandrosyl)-α-L-oleandrosyl, 4"-acyl-4'-(α-L-oleandrosyl)-α-L-oleandrosyl;
provided that at least one of the R, $R_1$ or $R_3$ groups contains an acyl group, and further that said acyl and the acyl portion of said acyloxy group is selected from loweralkanoyl; substituted loweralkanoyl wherein the substituents are halogen, carboxy, loweralkoxycarbonyl, amino, mono- or di-loweralkylamino, or loweralkanoylamino; unsaturated loweralkanoyl, loweralkoxycarbonyl, halogenated loweralkoxycarbonyl, benzoyl, or substituted benzoyl in which the substituents are halogen, nitro, alkyl, amino, hydroxy or alkoxy; carbamoyl, and N-substituted and N,N-disubstituted carbamoyl wherein the substitution is loweralkyl, benzyl, hydroxyloweralkyl or the carbamoyl nitrogen may be incorporated into a morpholine heterocycle.

2. The compound of claim 1 in which $R_2$ is iso-propyl.
3. The compound of claim 1 in which $R_2$ is sec-butyl.
4. The compound of claim 3 in which the acyl substituent is loweralkanoyl.
5. The compound of claim 4 in which the loweralkanoyl group is acetyl or propionyl.
6. The compound of claim 5 in which the acetyl or propionyl group is at the 4" position.
7. The compound of claim 5 in which the acetyl or propionyl group is at the 4" and 23 positions.
8. The compound of claim 5 in which the acetyl or propionyl group is at the 4" and 5 positions.
9. The compound of claim 6 which is C-076 A1a 4"-O-acetate wherein R is 4"-O-acetate-4'-(α-L-oleandrosyl)-α-L-oleandrosyl; $R_1$ is a 22,23 double bond; $R_2$ is sec butyl; and $R_3$ is methoxy.
10. The compound of claim 6 which is C-076 A2a 4"-O-acetae wherein R is 4"-O-acetate-4'-(α-L-oleandrosyl)-α-L-oleandrosyl; $R_1$ is hydroxy; $R_2$ is sec butyl; and $R_3$ is methoxy.
11. The compound of claim 6 which is C-076 B1a 4"-O-acetate wherein R is 4"-O-acetate 4'-(α-L-oleandrosyl)-α-L-oleanrosyl; $R_1$ is a 22,23 double bond; $R_2$ is sec butyl; and $R_3$ is hydroxy.

12. The compound of claim 6 which is C-076 B2a 4″-O-acetate wherein R is 4″-O-acetate 4′-(α-L-oleandrosyl)-α-L-oleandrosyl; $R_1$ is hydroxy; $R_2$ is sec butyl; and $R_3$ is hydroxy.

13. The compound of claim 7 which is C-076 A2a 4″,23, di-O-acetate wherein R is 4‴-O-acetate 4′-(α-L-oleandrosyl)-α-L-oleandrosyl; $R_1$ is acetoxy; $R_2$ is sec butyl; and $R_3$ is methoxy.

14. The compound of claim 8 which is C-076 B1a 4″,5-di-O-acetate wherein R is 4″-O-acetate-4′-(α-L-oleandrosyl)-α-L-oleandrosyl; $R_1$ is a 22,23 double bond, $R_2$ is sec butyl; and $R_3$ is acetoxy.

15. The compound of claim 8 which is C-076 B2a 4″,5-di-O-acetate wherein R is 4″-O-acetate-4′-(α-L-oleandrosyl)-α-L-oleandrosyl; $R_1$ is hydroxy; $R_2$ is sec butyl and $R_3$ is acetoxy.

16. The compound of claim 8 which is C-076 B1a-5-O-acetate wherein R is 4′-(α-L-oleandrosyl)-α-L-oleandrosyl; $R_1$ is a 22,23 double bond; $R_2$ is sec butyl; R and $R_3$ is acetoxy.

* * * * *